United States Patent [19]

Hassett

[11] Patent Number: 5,110,473
[45] Date of Patent: May 5, 1992

[54] METHOD AND APPARATUS FOR SAMPLING ORGANIC COMPOUNDS IN WATER

[75] Inventor: John P. Hassett, Cortland, N.Y.
[73] Assignee: The Research Foundation of State University of New York, Albany, N.Y.
[21] Appl. No.: 583,525
[22] Filed: Sep. 17, 1990
[51] Int. Cl.$^5$ .................. B01D 11/00; B01D 61/00
[52] U.S. Cl. ..................... 210/634; 210/637; 210/638; 210/651; 210/653; 210/654; 210/908; 210/909; 210/295
[58] Field of Search ............. 210/650, 634, 637, 638, 210/649, 650, 651, 653, 654, 500.21, 500.27, 908, 909, 500.23, 641, 490, 295; 436/178

[56] References Cited

U.S. PATENT DOCUMENTS

| | | | |
|---|---|---|---|
| 4,163,713 | 8/1979 | Keogh | 210/500.36 |
| 4,477,354 | 10/1984 | Fessier | 210/909 |
| 4,775,476 | 10/1988 | Melcher et al. | 210/635 |
| 4,844,745 | 7/1989 | Nash et al. | 210/909 |
| 4,869,825 | 9/1989 | Steiner | 210/908 |
| 4,886,603 | 12/1989 | Taylor | 210/641 |
| 4,912,051 | 3/1990 | Zaromb | 436/178 |
| 4,913,821 | 4/1990 | Melcher et al. | 210/635 |

OTHER PUBLICATIONS

Melcher, R. G., Analytica Chimica Acta. 214:299–313 (1988).
Sodergren, A., Environ. Sci. Technol. 21:855–859 (1987), No. 9.

Primary Examiner—Frank Spear
Assistant Examiner—Ana Fortuna
Attorney, Agent, or Firm—Heslin & Rothenberg

[57] ABSTRACT

The subject invention is directed to an apparatus for removing organic compounds from water which comprises: a housing having an opening therein, the housing being capable of retaining an organic solvent therein; and a nonporous membrane covering the opening, the membrane being capable of allowing organic compounds from the water to diffuse therethrough. The subject invention also provides method of removing organic compounds from water and a method for detecting the presence or determining the amount of organic compounds in the water.

17 Claims, 1 Drawing Sheet

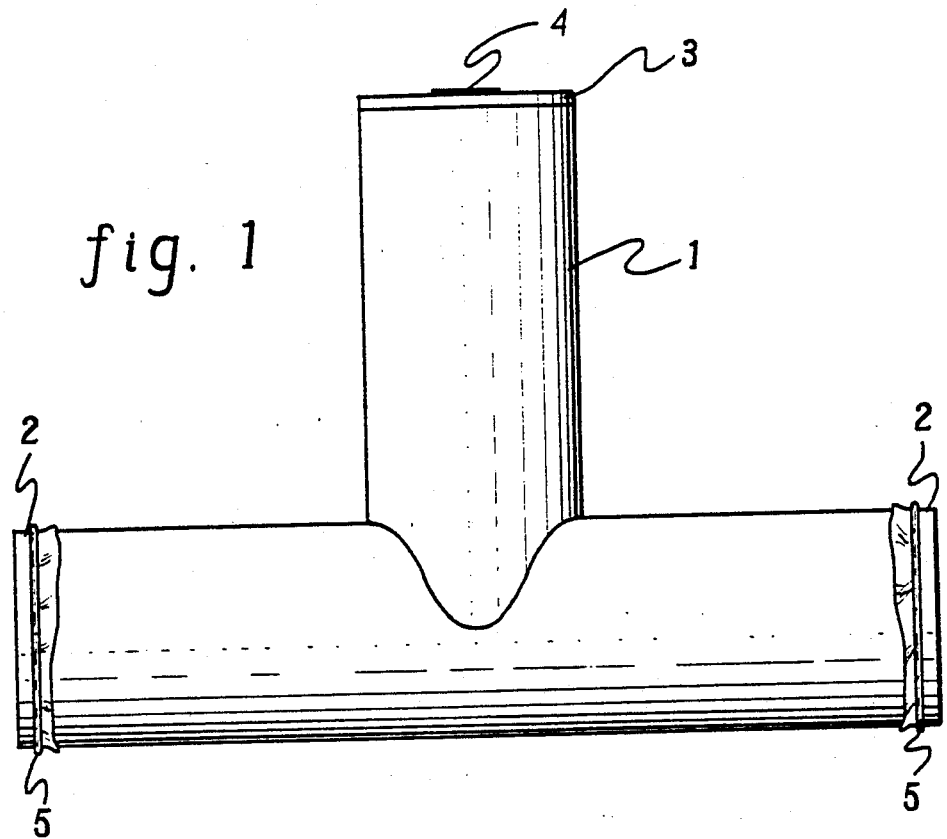
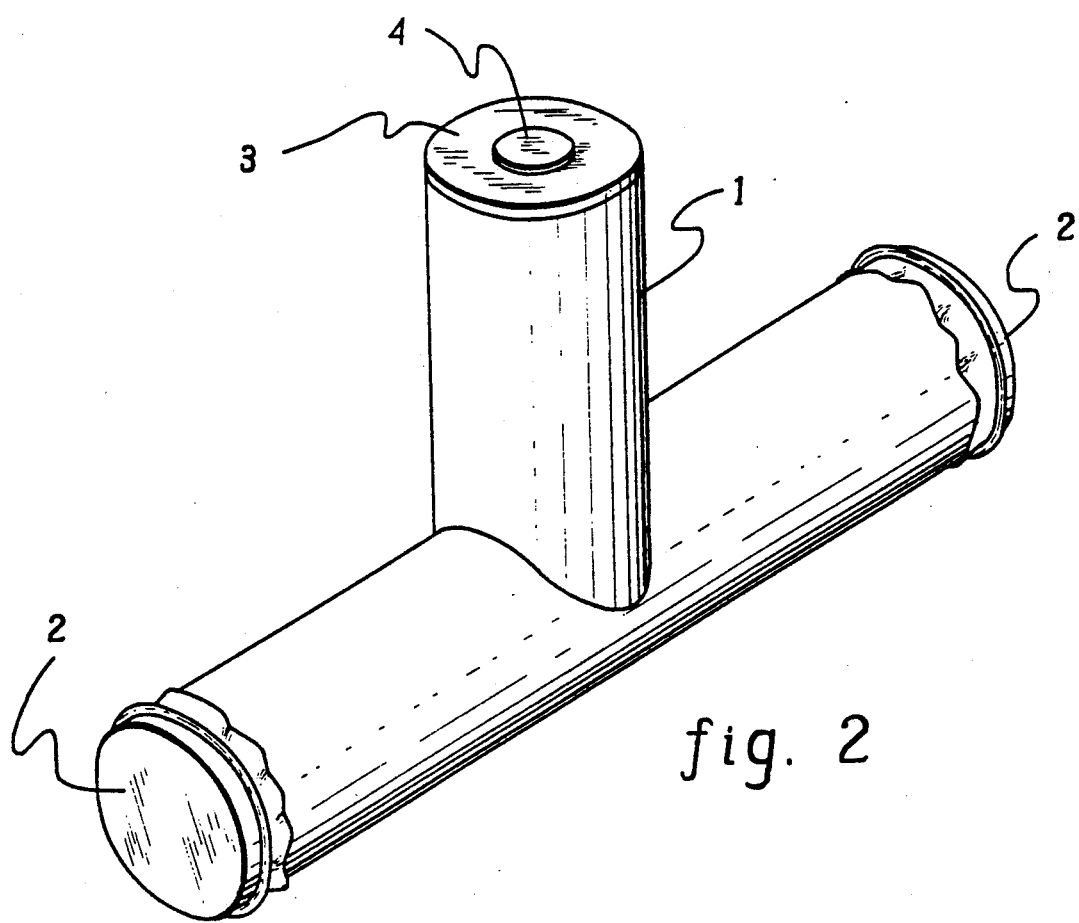

METHOD AND APPARATUS FOR SAMPLING ORGANIC COMPOUNDS IN WATER

FIELD OF THE INVENTION

The subject invention is directed to an apparatus for removing organic compounds from water, including hydrophobic organic compounds such as polychlorinated biphenyls (PCBs), polynuclear aromatic hydrocarbons (PAHs), dioxins, petroleum materials, and pesticides. In addition to removing the organic compounds from water, the subject apparatus can be used in detecting the presence of and determining the amount of such organic compounds in the water.

BACKGROUND OF THE INVENTION

Considering the present environmental problems involving both waste disposal and its effect upon the quality of water, it is necessary to test groundwater, surface water, water supplies, waste water and/or industrial liquid waste to determine the concentration of any contaminants therein. It is desirable to determine the concentration of organic compounds in water so that the deleterious effects of these contaminants can be minimized, thereby maintaining and improving the quality of our water supplies. Many non-purgable hydrophobic organic compounds are known to contaminate water supplies. Polychlorinated biphenyls (PCBs), polynuclear aromatic hydrocarbons (PAHs), dioxins, petroleum materials, and pesticides, for example, are just some of these commonly known organic compounds.

There are currently available modern analytical instruments which are capable of detecting and quantifying minute amounts of organic compounds. Presently, however, the testing of water for the presence of organic compounds is commonly performed by transporting samples of water to various testing apparatuses, usually located in a laboratory. This procedure, however, is labor intensive.

One problem with the current testing and measurement of organic compounds in water is that the concentration of these organic compounds in water may be minute, making it difficult for analytical devices to accurately measure the concentration levels. As a result, it is frequently necessary to increase the concentration of the organic compounds in order to measure their concentration. This is accomplished by performing an extraction process in the laboratory, which may increase the cost of water analysis and also increase the labor involved in such analysis.

It is, therefore, an object of the present invention to provide a method and apparatus for an inexpensive and simple determination of the presence and amount of organic compounds in water without the necessity of transporting a sample of the water to a laboratory. In this manner, larger water samples can be analyzed which will improve detection limits.

It is also an object of the subject invention to provide a method and apparatus which eliminate the extraction process normally performed in a laboratory.

The subject invention accomplishes these objectives by providing a method and apparatus for removing organic compounds from water in-situ. The organic compounds are collected in a solvent retained within an apparatus having non-porous membranes, and such solvent can then be analyzed directly within a laboratory. This eliminates the extraction step in the laboratory analysis of most water samples, thus potentially decreasing the cost of water analysis.

The subject invention further provides an apparatus which will greatly enhance the effectiveness of field monitoring programs by allowing collection of more samples and the achievement of better detection limits on the samples collected. This is because the subject apparatus can be placed in water and left there for a much longer amount of time, allowing for larger water samples to be analyzed.

Sodergren, A., Environ. Sci. Technol. 21 855-859 (1987) discloses a solvent-filled dialysis membrane which simulates the uptake of pollutants by aquatic organisms. Sodergren uses dialysis membranes filled with hexane to accumulate persistent lipophilic pollutants in a way similar to that of aquatic organisms.

SUMMARY OF THE INVENTION

The subject invention provides an apparatus for sampling organic compounds in water by removing such organic compounds from the water which comprises: a housing having an opening therein, the housing being capable of retaining an organic solvent therein; and a non-porous membrane covering the opening, the membrane being capable of allowing organic compounds from the water to diffuse therethrough.

The subject invention further provides a method for removing organic compounds from water which comprises: placing the subject apparatus in water, the apparatus containing an organic solvent; allowing the organic compounds in the water to diffuse through the membrane into the organic solvent contained within the housing; and removing the apparatus from the water, thus removing the organic compounds in the organic solvent from the water. Further provided are methods for detecting the presence of organic compounds in water and methods for determining the amount of organic compounds in water.

BRIEF DESCRIPTION OF THE FIGURES

These and other objects, features and advantages of the invention will be evident from the following detailed description when read in conjunction with the accompanying drawings in which:

FIG. 1 is a side view showing a preferred apparatus of the subject invention for removing organic compounds from water.

FIG. 2 is a perspective view of the apparatus of FIG. 1.

DETAILED DESCRIPTION OF THE INVENTION

The subject invention provides an apparatus for removing organic compounds from water which comprises: a housing having an opening therein; the housing being capable of retaining an organic solvent therein; and a non-porous membrane covering the opening, the membrane being capable of allowing organic compounds from the water to diffuse therethrough. The organic compounds which can be removed from water using the subject apparatus are hydrophobic, i.e. they lack an affinity for water. These include polychlorinated biphenyls (PCBs), polynuclear aromatic hydrocarbons (PAHs), dioxins, petroleum materials, and pesticides.

These organic compounds can be extracted from the water using an organic solvent which is retained within the housing. The organic solvent is hexane or octane, preferably, although other organic solvents may also be used. The non-porous membrane covering the opening of the housing must be capable of allowing organic compounds from the water to diffuse therethrough. Its non-porous nature, however, prevents the water from entering the housing. Preferably, the non-porous membrane is made from a polymer, such as polyethylene. Polyethylene membranes preferably have a diameter of 2.5–3.8 cm and are 0.025 mm thick.

The subject apparatus is placed within water and may be left there for up to one month, for example. As dissolved gases from the water accumulate within the housing, pressure may build up. Therefore, in a preferred embodiment of the subject invention, the apparatus additionally comprises a means for reducing pressure within the housing. This prevents the membranes from bursting or disconnecting from the housing. This means for reducing pressure is preferably a pressure relief valve which can open or be opened to release pressure within the apparatus.

A preferred structure of the apparatus of the subject invention is illustrated in FIGS. 1 and 2. The apparatus comprises a tubular T member as a housing (1) having non-porous polyethylene membranes (2) covering the first and second openings of the cross portion of the T, and a cap (3) located atop the middle opening of the T member which includes a pressure relief valve (4) for releasing pressure within the device. The tubular T member (1) can be made of any suitable material including glass or chrome-plated brass. The T member may be an inch and one half standard plumbing T member.

Suitable non-porous membranes are 2.5 cm diameter $\times 0.025$ mm thick membranes (4.9 cm$^2$ area) or dual 3.8 cm diameter $\times 0.025$ mm thick membranes (23 cm$^2$ total area). These membranes are connected to the T member preferably by means of a rubber O-ring sealing means (5). However, the membranes could also be connected by holding them in a sandwich between two plates. The entire device is inserted into water which may be in a bore-hole, a well, a stream, or in a lake or the like. Organic compounds present in the water diffuse through the membranes and remain in the organic solvent. A cap can be threaded onto the middle opening of the T member, so that an organic solvent solution, for example hexane or octane, can fill the T member.

The apparatus of the subject invention can be used in a method for removing organic compounds from water which comprises: placing the apparatus in water, the apparatus containing an organic solvent; allowing the organic compounds in the water to diffuse through the membrane into the organic solvent contained within the housing; and removing the apparatus from the water, thus removing the organic compounds in the organic solvent from the water.

The method can further comprise concentrating the organic compounds which are removed from the water by removing the organic solvent from the apparatus and then concentrating the extract, for example by evaporation.

Further provided is a method of detecting the presence of organic compounds in water which comprises placing the apparatus in water, the apparatus containing an organic solvent; allowing any organic compounds in the water to diffuse through the membrane into the organic solvent contained within the housing; removing the apparatus from the water, thus removing any organic compounds in the organic solvent from the water; and detecting the presence of any organic compounds in the organic solvent thus removed.

Further provided is a method of determining the amount of organic compounds in water which comprises: placing the apparatus in water, the apparatus containing an organic solvent; allowing any organic compounds in the water to diffuse through the membrane into the organic solvent contained within the housing; removing the apparatus from the water, thus removing any organic compounds in the organic solvent from the water, and determining the amount of any organic compounds in the organic solvent thus removed.

Conventional techniques for determining the presence or amount of organic compounds in the organic solvent can be used. These include gas chromatography and ultraviolet absorption techniques.

EXAMPLE 1

The subject invention thus provides a passive, i.e., no moving parts, apparatus for in-situ sampling of organic compounds in water. This sampler consists of a metal body holding two 11.5 cm$^2$ polyethylene membranes. The sampler is filled with an organic solvent, hexane, and suspended in the water body to be sampled. Sampling occurs by diffusion of dissolved organic compounds from the water through the membranes and accumulation in the solvent. Effective sampling rates for polychlorinated biphenyls, PCB's, are 0.75–1.4 L/day, over the temperature range of 5° to 25° C. Reproducibility in field trials is $\pm$ 10% standard deviation.

Field exposures up to four weeks have been accomplished.

These sampling rates of about 1 liter per day (L/day) for PCB's and field exposure times of up to 28 days allow effective sampling of large volumes of water without having to pump or transport water samples. The device provides a sample already in organic solvent, thus eliminating the extraction step in laboratory analysis. The apparatus thus greatly enhances the effectiveness of field monitoring programs by allowing collection of more samples and achievement of better detection limits on the samples collected. Field trials have already shown the utility of the samplers in identifying pollutant sources where conventional water sampling has failed.

EXAMPLE 2

A passive, in-situ concentration/extraction sampler (PISCES) for hydrophobic organic compounds in water has been developed. Sampling is based on adsorption of a hydrophobic solute from water onto the surface of a nonporous polymer membrane, diffusion through the membrane and collection in an organic solvent reservoir. The flux of organic compounds through the membrane may be represented by the equation:

$$J = (DA/L)(K_{mw}C_w - K_{ms}C_s)$$

where J is the flux (mole/min), D is the diffusion coefficient (cm$^2$/min) of the organic compound, A is the surface area of the membrane (cm$^2$), L is the thickness of the membrane (cm), $K_{mw}$ and $K_{ms}$ are the membrane-water and membrane-solvent partition coefficients respectively (unitless), and $C_w$ and $C_s$ are the concentrations of the organic compounds in the water and solvent, respectively (mol/cm$^3$). If the value of $K_{mw}C_w$ is much greater (typically 10 times greater) than the value of $K_{ms} C_s$ (the solvent does not approach equilibrium with the water), the flux of organic compounds through the membrane may be represented by:

$$J = (DA\ K_{mw}/L)C_w$$

or, combining the constants:

$$J = D \cdot C_w$$

The quantity $D*$ is the effective sampling rate (e.g., L/day) of the sampler apparatus. It is potentially a function of temperature, the diffusing compound, the reservoir solvent and the membrane composition, thickness and area. The above equation indicates that the amount of a compound collected by the sampler apparatus over a given period of time will be a function of the average concentration of that compound in the water over the time period. Therefore, PISCES offers the possibility of long-term, unattended, integrating sampling.

Polyethylene membranes were chosen for sampler development because they have a combination of good diffusion characteristics, mechanical strength and availability. Hexane was chosen as the receiving solvent because it does not interfere with gas chromatography electron capture detection, does not diffuse out of the sampler too fast and can be easily evaporated for sample concentration. Laboratory studies were carried out at controlled temperatures using the PCB mixture Aroclor 1242 to provide a range of test compounds. Samplers with glass bodies and 2.5 cm diam. $\times$ 0.025 mm thick membranes (4.9 cm$^2$ area) were used for lab studies. Field samplers were constructed of chrome-plated brass and contained dual membranes each 3.8 cm diam. $\times$ 0.025 mm thick (23 cm$^2$ total area). Field studies were carried out on the Hudson River in an area contaminated by PCBs. Samplers were evaluated for reproducibility, durability and practicality.

Sampling rate for PCBs dissolved in distilled water is independent of PCB structure but is dependent on temperature. Sampling rate for the congeners 2,4'-dichlorobiphenyl, 2,4,4'-trichlorobiphenyl and 2,3,3',4',6-pentachlorobiphenyl is given by:

$$sampling\ rate\ (L/day/cm^2) = 0.0015T + 0.025$$

where T is the temperature in degrees Celsius. This gives sampling rates for the field sampler (23 cm$^2$ membrane area) of 0.75 L/day at 5° C. and 1.4 L/day at 25° C.

Field trials indicate that biofouling of the membrane is not a problem. Slow diffusion of hexane through the membrane apparently inhibits microorganisms from colonizing its surface. However, diffusion of hexane out of the sampler limits the duration of exposure. At about 25° C., samplers could be exposed in the field for up to 3 weeks before too much hexane (about 120 mL) was lost. Exposure periods could be lengthened by increasing the reservoir size or by using a slower-diffusing solvent such as octane. At low temperatures (about 5° C.), little hexane was lost after the longest exposure, 4 weeks.

PISCES were deployed in pairs in the Hudson River. PCBs could be detected in the samplers after as little as 8 hour exposure, and in all cases after 24 hour exposure. Standard deviation and coefficient of variation were calculated from 26 pairs. The average coefficient of variation for 9 PCB congeners was 12%, which was comparable to results obtained by conventional liquid-liquid extraction.

Although the subject invention has been described with regard to the embodiments disclosed herein, variations in the invention may be made without departing from the spirit of the invention. Any such variations are intended to be within the scope of the invention as defined by the following claims.

I claim:

1. An apparatus for removing organic compounds from water which comprises:
    a housing having an opening therein, the housing being capable of retaining an organic solvent therein;
    a nonporous membrane covering the opening, the membrane being capable of allowing organic compounds from the water to diffuse therethrough; and
    a means for reducing pressure in the housing.

2. The apparatus of claim 1 wherein the organic solvent is hexane.

3. The apparatus of claim 1 wherein the organic solvent is octane.

4. The apparatus of claim 1 wherein the membrane is a nonporous polymer membrane.

5. The apparatus of claim 4 wherein the nonporous polymer membrane is a polyethylene membrane.

6. The apparatus of claim 5 wherein the polyethylene membrane is 2.5-3.8 cm in diameter and 0.025 mm thick.

7. The apparatus of claim 1 wherein the means for reducing pressure in the housing comprises a pressure relief valve.

8. The apparatus of claim 1 wherein the housing comprises a T member having a middle opening and a first and second opening.

9. The apparatus of claim 8 wherein a cap is placed on the middle opening for addition of an organic solvent to the housing.

10. The apparatus of claim 9 wherein the cap contains a means for reducing pressure in the housing.

11. The apparatus of claim 10 wherein the means for reducing pressure comprises a pressure relief valve.

12. A method for removing organic compounds from water in situ which comprises the steps of:
    a) placing an apparatus for removing organic compounds from water in water in situ, the apparatus comprising a housing having an opening therein, a nonporous membrane covering the opening, and a means for reducing pressure in the housing, the apparatus containing an organic solvent and the membrane being capable of allowing organic compounds from the water to diffuse therethrough;
    b) allowing the organic compounds in the water to diffuse through the membrane into the organic solvent contained within the housing;
    c) reducing any pressure within the housing; and
    d) removing the apparatus from the water, thus removing the organic compounds in the organic solvent from the water.

13. The apparatus of claim 12 wherein the organic compounds comprise polychlorinated biphenyls.

14. A method of claim 12, wherein the organic compounds removed from the water are concentrated.

15. A method of claim 14, wherein the organic compounds are concentrated by evaporation of the organic solvent.

16. A method of detecting the presence of organic compounds in water in situ which comprises the steps of:
   a) placing an apparatus for removing organic compounds from water in water in situ, the apparatus comprising a housing having an opening therein, a nonporous membrane covering the opening, and a means for reducing pressure in the housing, the apparatus containing an organic solvent and the membrane being capable of allowing organic compounds from the water to diffuse therethrough;
   b) allowing any organic compounds in the water to diffuse through the membrane into the organic solvent contained within the housing;
   c) reducing any pressure within the housing;
   d) removing the apparatus from the water, thus removing any organic compounds in the organic solvent from the water; and
   e) detecting the presence of any organic compounds in the organic solvent thus removed.

17. A method of determining the amount of organic compounds in water in situ which comprises the steps of:
   a) placing an apparatus for removing organic compounds from water in water in situ, the apparatus comprising a housing having an opening therein, a nonporous membrane covering the opening, and a means for reducing pressure in the housing, the apparatus containing an organic solvent and the membrane being capable of allowing organic compounds from the water to diffuse therethrough;
   b) allowing any organic compounds in the water to diffuse through the membrane into the organic solvent contained within the housing;
   c) reducing any pressure within the housing;
   d) removing the apparatus from the water, thus removing any organic compounds in the organic solvent from the water; and
   e) determining the amount of any organic compounds in the organic solvent thus removed.

* * * * *